United States Patent [19]

Morgan et al.

[11] Patent Number: 5,479,021

[45] Date of Patent: Dec. 26, 1995

[54] TRANSMISSION LINE SOURCE ASSEMBLY FOR SPECT CAMERAS

[75] Inventors: Hugh T. Morgan, Highland Heights; Bryce G. Thornton, Concord, both of Ohio

[73] Assignee: Picker International, Inc., Highland Hts., Ohio

[21] Appl. No.: 155,015

[22] Filed: Nov. 19, 1993

Related U.S. Application Data

[63] Continuation-in-part of Ser. No. 27,882, Mar. 8, 1993, Pat. No. 5,338,936, which is a continuation-in-part of Ser. No. 712,676, Jun. 10, 1991, Pat. No. 5,210,421.

[51] Int. Cl.$^6$ .................... G01T 1/00; G21K 5/00; G21F 3/00
[52] U.S. Cl. .................... 250/363.04; 250/498.1
[58] Field of Search ............ 250/363.04, 496.1, 250/498.1, 503.1, 505.1; 378/147, 156

[56] References Cited

U.S. PATENT DOCUMENTS

| | | | |
|---|---|---|---|
| 3,177,364 | 4/1965 | Green | 250/498.1 |
| 4,472,827 | 9/1984 | Gabbay et al. | 378/140 |
| 5,033,074 | 7/1991 | Cotter et al. | 378/147 |
| 5,033,075 | 7/1991 | DeMone et al. | 378/156 |

FOREIGN PATENT DOCUMENTS

| | | |
|---|---|---|
| 0056552 | 7/1982 | European Pat. Off. . |
| 0279476 | 8/1988 | European Pat. Off. . |
| 0526970 | 2/1993 | European Pat. Off. . |
| 3-67194 | 3/1991 | Japan ............... 250/363.04 |

OTHER PUBLICATIONS

"Fast Transmission CT For Determining Attenuation Maps Using a Collimated Line Source, Rotatable Air–Copper–Lead Attenuators and Fan–Beam Collimation", Jaszczak, et al., *J. Nucl. Med.*, vol. 34, No. 9, Sep. 1993 pp. 1577–1579.

*Primary Examiner*—Constantine Hannaher
*Attorney, Agent, or Firm*—Fay, Sharpe, Beall, Fagan, Minnich & McKee

[57] ABSTRACT

A rotatable gantry portion (16) is rotatably mounted on the stationary gantry portion (18) of a SPECT camera. A plurality of radiation detector heads (10a, 10b, 10c) are mounted to the rotating gantry. A transmission radiation source holder and collimator assembly (40, 42) is mounted to the rotatable gantry portion opposite one of the detector heads. A transmission radiation source (60) is mounted in a lead shield (62) with an opening (64) pointing toward an examination region (12). A shutter (66) is rotatable between a closed position in which a lead arc segment (70) blocks the opening (64), a calibration orientation in which tin (72) covers opening (64), and an open position in which an opening (74) is aligned with the opening (64). A safety interlock means (80) locks the shutter in the closed position and against rotation when the radiation source holder is removed from the rotatable gantry portion. A collimator (42) has lead side walls (200) and tin or tin alloy septa (202). When radiation from the radiation source strikes the lead side walls, they emit characteristic lead x-rays of about 88 keV whereas the tin radiates x-rays of only about 30 keV. A filter (210) includes an inner layer (212) of tin for attenuating any remaining 88 keV lead x-rays coming from the transmission line source assembly and converting them to about 30 keV radiation. The filter has an outer layer (214) for attenuating the radiation around 30 keV.

47 Claims, 5 Drawing Sheets

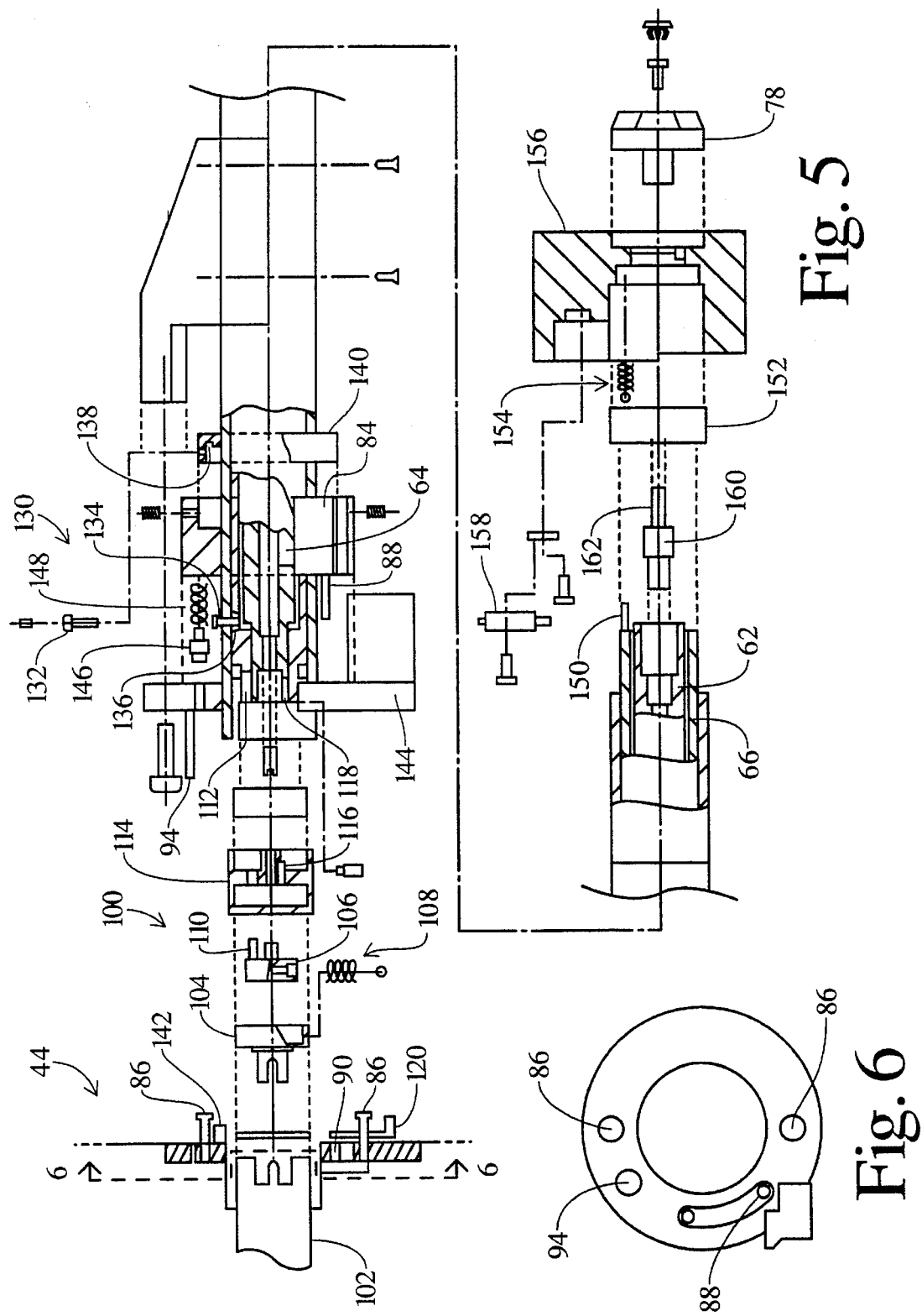

TRANSMISSION LINE SOURCE ASSEMBLY FOR SPECT CAMERAS

This application is a continuation-in-part of U.S. application Ser. No. 08/027,882 filed Mar. 8, 1993, which, in turn, is a continuation-in-part of U.S. application Ser. No. 07/712,676 filed Jun. 10, 1991, now U.S. Pat. No. 5,210,421.

BACKGROUND OF THE INVENTION

The present invention relates to the art of diagnostic imaging. It finds particular application in conjunction with single-photon emission computed tomography (SPECT) systems which include one or more transmission radiation line sources and will be described with particular reference thereto. It is to be appreciated, however, that the invention will also find application in conjunction with other types of nuclear medicine and transmission radiation diagnostic imagers.

Heretofore, single photon emission computed tomography has been used to study the radionuclei distribution in subjects. Typically, one or more radiopharmaceuticals were injected into a patient's blood stream for imaging the circulatory system or specific organs which absorb the injected radiopharmaceuticals. One or more gamma or scintillation camera heads were placed closely adjacent to a surface of the patient to monitor and record radiation emitted by the radiopharmaceuticals. In single photon emission computed tomography, the heads were rotated or indexed around the subject to monitor the emitted radiation from a multiplicity of directions. The data monitored from the multiplicity of directions was reconstructed into a three-dimensional image representation of the radiopharmaceutical distribution within the patient.

One of the problems with the SPECT imaging technique is that the patient is not completely homogeneous in terms of radiation attenuation or scatter. Rather, the human patient includes many different tissue and bone types which absorb or scatter radiation from the radiopharmaceuticals to different degrees. The SPECT images can be made more accurate if they are corrected for the radiation lost to scattering or attenuation along each path through the human torso.

As described in our parent U.S. Pat. No. 5,210,421, a radiation line source can be positioned opposite one or more of the gamma or scintillation camera heads. Transmission radiation from the line source received by the opposite detector head can be reconstructed into a three-dimensional image representation of the radiation absorptive properties of each incremental volume element of the patient, analogous to a CT scan. This radiation attenuation information is utilized to correct the SPECT data. When the radiation line source and the radiopharmaceuticals have distinctly different energy peaks, the transmission radiation and photon emission radiation image data can be collected concurrently and separated based on energy.

One concern of the prior art line sources was in operator safety. The line sources typically include a tube filled with a radionucleide material which is emitting radiation continuously. There is no radiation generating "chemical reaction" that can be started and stopped. The prior art line sources lacked a fail-safe system for assuring that the operator would not be subject to unnecessary radiation, particularly while the line source was being mounted to or removed from the scanner.

There has also been a disposal problem with spent radiation line sources. The strength of the radiation source decreases exponentially with time. At the half-life of the radioisotope, the radiation source is about ½ strength. Typically, after a 50% reduction in line source strength, about one half-life, the radioisotope tube was replaced.

In the prior art, collimators were typically constructed of lead. When lead is struck with incident radiation, such as the radiation from the line source, the lead emits an x-ray with a characteristic energy of about 88 keV. The 88 keV x-ray has an energy which is sufficiently close to the emission energy of some common radiopharmaceuticals that it is difficult to distinguish the two. This inability to distinguish reliably radiation from the radiopharmaceuticals and radiation emitted from the lead caused errors in the resultant radiopharmaceutical image.

One solution for separating the lead x-rays coming from the line source assembly from the radiation emitted from the radiopharmaceuticals was to conduct the line source transmission radiation examination first. The transmission line source was removed or closed before the radiopharmaceuticals were injected and imaged. However, performing the transmission examination and the radiopharmaceutical diagnostic examination sequentially lead to registration problems. The transmission radiation data and radiopharmaceutical images data frequently became at least partially misaligned. This misalignment caused incorrect transmission radiation based corrections on the radiopharmaceutical data causing further image degradation.

The present application provides a new and improved transmission line source assembly which overcomes the above-referenced problems and others.

SUMMARY OF THE INVENTION

In accordance with one aspect of the present invention, the line source includes a shutter assembly. The shutter assembly is movable between a closed position in which radiation is prevented from being emitted from the line source, a calibration position in which limited or filtered radiation is emitted, and a full open position.

In accordance with another aspect of the present invention, a safety lock is provided in which the shutter is locked against being moved from the closed position unless the line source assembly is mounted to a gamma camera gantry.

In accordance with another aspect of the present invention, the shutter is movable between its open, closed, and calibration states electromechanically from a software controlled or remote operator location.

In accordance with another aspect of the present invention, an electrical feedback system is provided for providing a positive indication of the actual state of the shutter.

In accordance with another aspect of the present invention, the line source assembly is not removable from the camera gantry unless the shutter is in its closed state.

In accordance with another aspect of the present invention, replacement of the transmission radiation line source tube requires a key such that only a key operator can gain access to the transmission line source.

In accordance with another aspect of the present invention, an interchangeable attenuator/filter is provided. As the radioisotope of the transmission line source decays, the attenuation/filter is replaced by a new attenuator/filter with reduced attenuation properties. In this manner, the radiation from the line source is held relatively constant over an extended duration of several half-lives.

In accordance with another aspect of the present invention, a collimator is provided which is constructed in substantial part of tin, antimony, zirconium, niobium, molybdenum, germanium, yttrium, cerium, gadolinium, terbium, dysprosium, holmium, erbium, ruthenium, rhodium, palladium, silver, cadmium, indium, tellurium, cesium, barium, and alloys thereof.

In accordance with a more limited aspect of the present invention, the collimator includes a multiplicity of septa which are constructed of the above-referenced metals or alloys thereof.

In accordance with another aspect of the present invention, the collimator is constructed at least in part of lead which emits 88 keV x-rays. The collimator includes a first filter layer of a material with good stopping power for 88 keV radiation, with relative transparency to higher energy radiation, and which emits x-rays of a relatively low energy.

In accordance with another aspect of the present invention, the first filter layer is constructed of tin, antimony, or alloys thereof.

In accordance with another aspect of the present invention, a second filter layer is provided, which second filter layer attenuate the lower energy gamma rays from the first filter layer substantially completely and which is substantially invisible to higher energy radiation from the line source.

In accordance with another more limited aspect of the present invention, the second filter layer includes aluminum, copper, or alloys thereof.

One advantage of the present invention is that it improves operator safety.

Another advantage of the present invention is that it extends the useful life of transmission line sources, reducing radioactive waste disposal problems.

Another advantage of the present invention is that it removes or reduces lead emitted x-rays which can interfere with or be confused with radiation from injected radioisotopes.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 5 is an exploded view of the line source holder; and,

FIG. 6 illustrates an interior view along section 6—6.

DETAILED DESCRIPTION OF THE PREFERRED EMBODIMENTS

Figure 1:
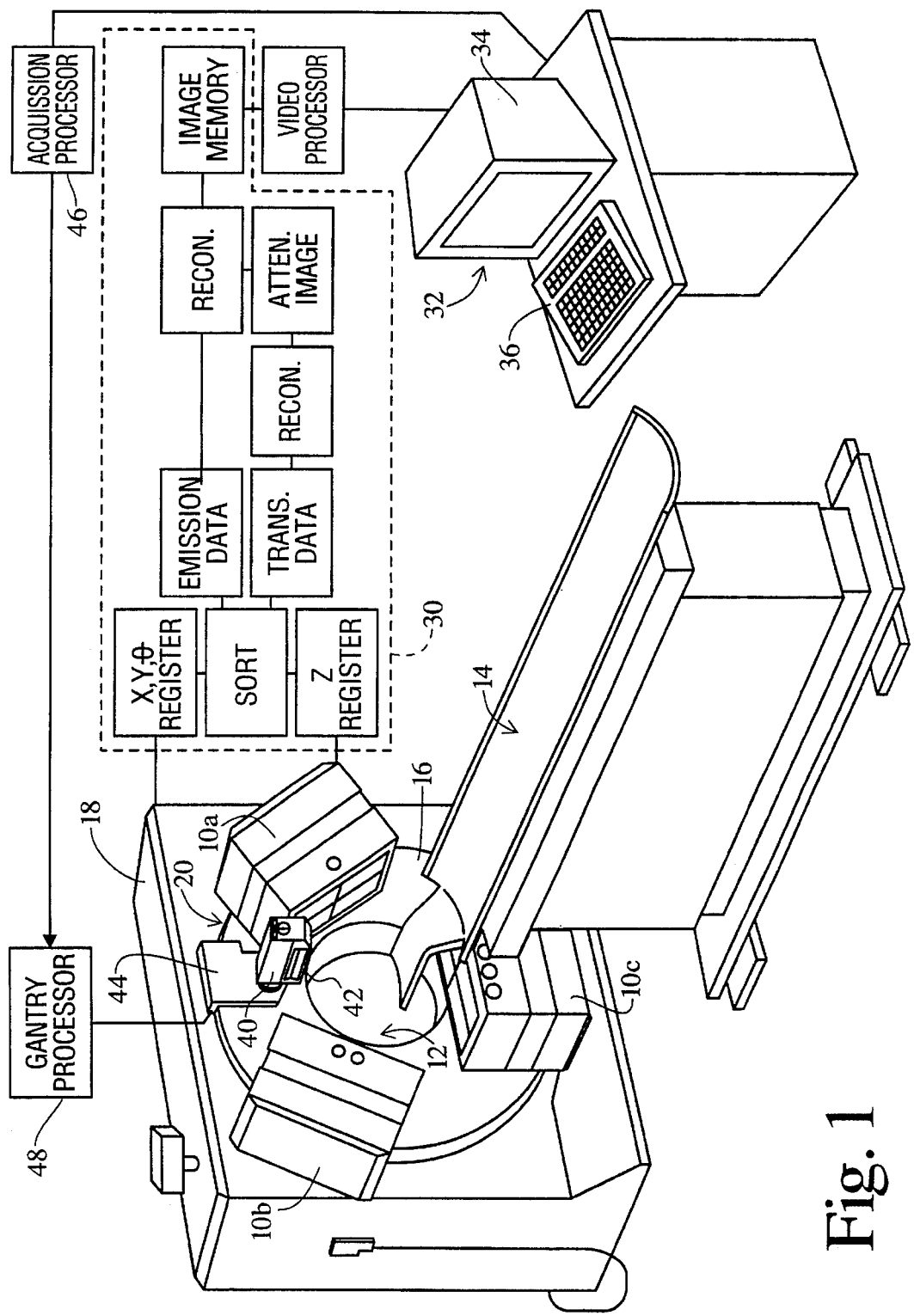
FIG. 1 is a perspective view of a SPECT camera system in accordance with the present invention.

With reference to FIG. 1, a SPECT camera assembly includes a plurality of gamma camera heads 10a, 10b, 10c, disposed equidistant around a subject examination region 12. A patient couch or other subject support 14 selectively supports a portion of an examined subject in the examination region.

The detector heads are mounted to a rotatable gantry portion 16 which is connected to a suitable motor and bearing assembly supported by a stationary gantry portion 18 to function as a means for rotating or indexing the detector heads around the examination region. Also mounted to the rotating gantry 16 are a plurality of mechanical drives (not shown) for moving each of the gamma camera heads independently radially toward and away from the examination region. The gamma camera heads are preferably mounted on roller carriages or slide bars for smoother, easier movement. The mechanical drives for moving the gamma camera heads radially preferably each include a motor that rotates a screw drive that engages a follower mounted to the gamma camera head.

Each camera head includes a scintillation crystal that responds to incident radiation by producing a flash of light. An array of photomultiplier tubes produce electrical signals in response to each light flash. The signals responsive to the scintillations or flashes of light are combined. The magnitude z of the resultant sum is indicative of the energy of the incident radiation. The relative response of the closest photomultiplier tubes is indicative of the spatial location x,y of the scintillation. An encoder (not shown) indicates the angular orientation θ of the receiving detector head around the examination region.

A transmission radiation source assembly 20 is also mounted on the rotating gantry portion 16. The transmission radiation source transmits radiation across the examination region 12 to an oppositely disposed detector head 10a. Optionally, additional transmission radiation sources may be disposed opposite others of the detector heads.

A reconstruction processor 30 processes the electrical signals from the detector heads as the detector heads are moved around the examination region to reconstruct a three-dimensional image representation.

Detected radiation from the transmission source is separated from detected radiation from the radiopharmaceutical on the basis of the energy z of the photon peaks. The reconstruction processing means 30 processes the transmission radiation to reconstruct a three-dimensional transmission radiation image representation indicative of the transmission radiation absorptive or blocking properties of the examined region of the subject. The transmission radiation information is used to corrected the reconstructed emission radiation image representation in the injected radiopharmaceuticals. The preferred reconstruction and correction processing is illustrated in greater detail in parent U.S. Pat. No. 5,210,421.

An operator control panel 32 includes a video monitor 34 for converting selected portions of the emission image representation into a human readable display. Optionally, transmission images might also be displayed. A keyboard 36 enables the operator to control the image reconstruction process, the selection of displayed data, the selection of preselected scanning procedures, and custom operation of the SPECT camera gantry. That is, the operator can control rotation of the rotatable gantry portion 16, movement of the detector heads radially toward and away from the examination region, and positioning of the patient couch 14.

Figure 2:
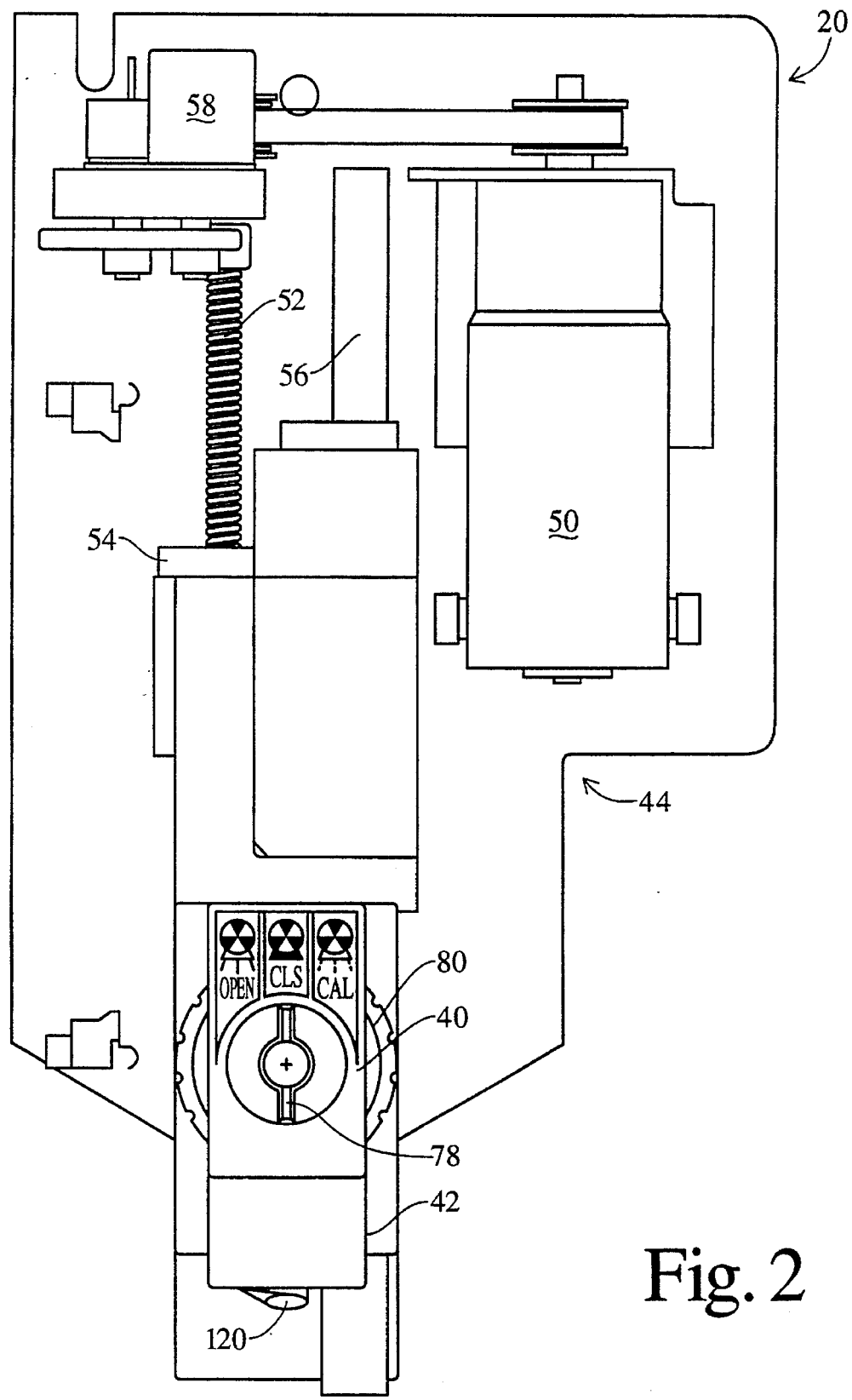
FIG. 2 is an enlarged end view of the line source assembly of FIG. 1 with a cover off the radial position adjusting mechanism.
Figure 3:
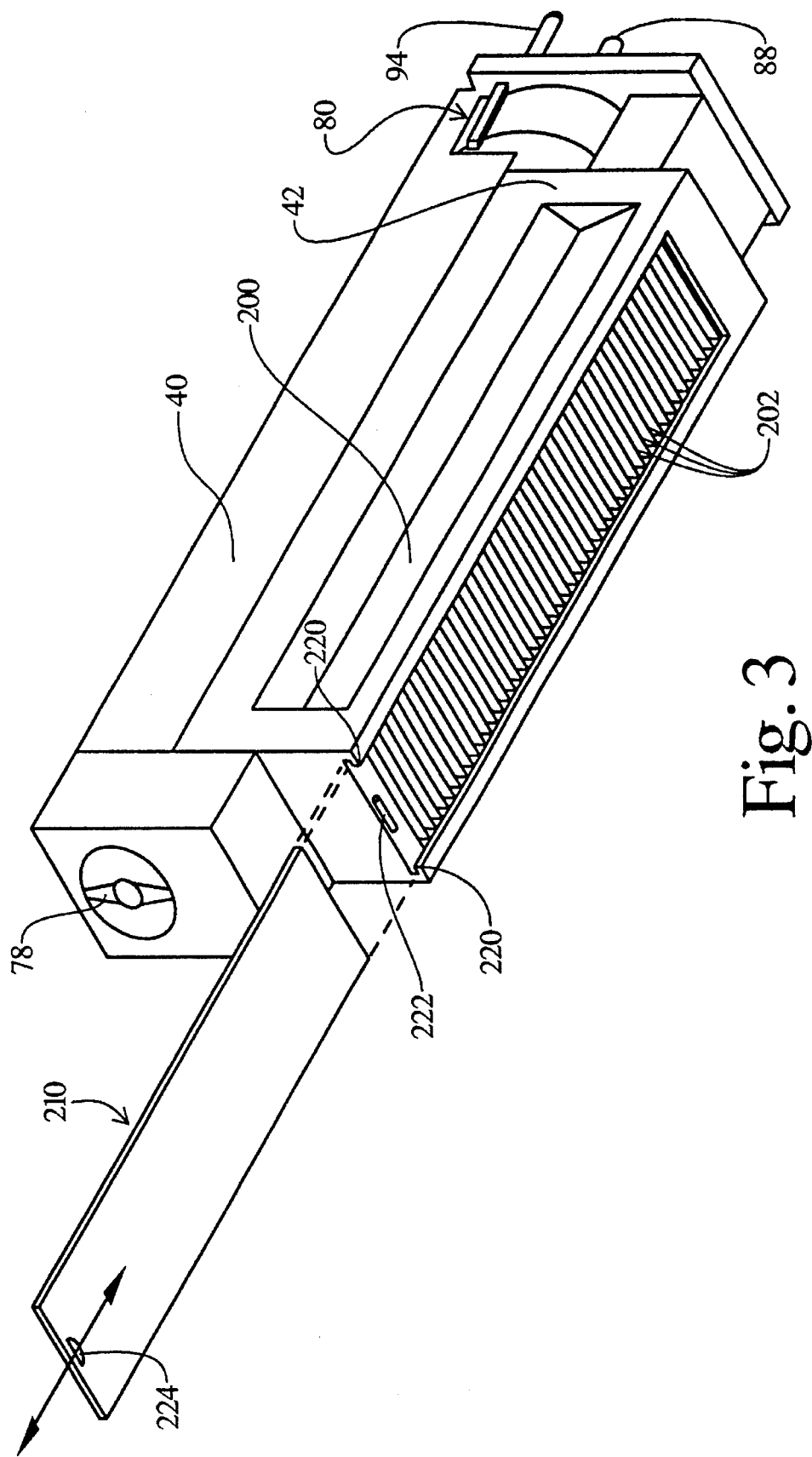
FIG. 3 is a perspective view of the line source assembly of FIG. 1 with the filter slid open to expose the collimator septa.

With continuing reference to FIG. 1 and further reference to FIGS. 2 and 3, the transmission radiation source 20 includes a transmission radiation source holder 40, a transmission radiation source collimator 42, and a means 44 for radially positioning the transmission radiation source. The operator through the console 32 selects a program routine from an acquisition processor 46. The acquisition processor supplies the initial information to a programmable gantry mounted processor 48. More specifically, a motor 50 selectively rotate a drive screw 52 that is received in a threaded drive 54 to which the radiation holder and collimator assembly is mounted. The motor 50 under control from the gantry processor 48 radially positions the transmission radiation source. For stability, the radiation source and collimator assembly are slidably mounted on a fixed rail 56 to insure accurate radial sliding movement. A spatial encoder 58 makes a precise determination of the radial position of the transmission radiation source holder and collimator assembly. Electromechanical controls controlled through the gantry processor 48 control opening and closing of the shutter for the transmission radiation source and other functions described below.

Figure 4:
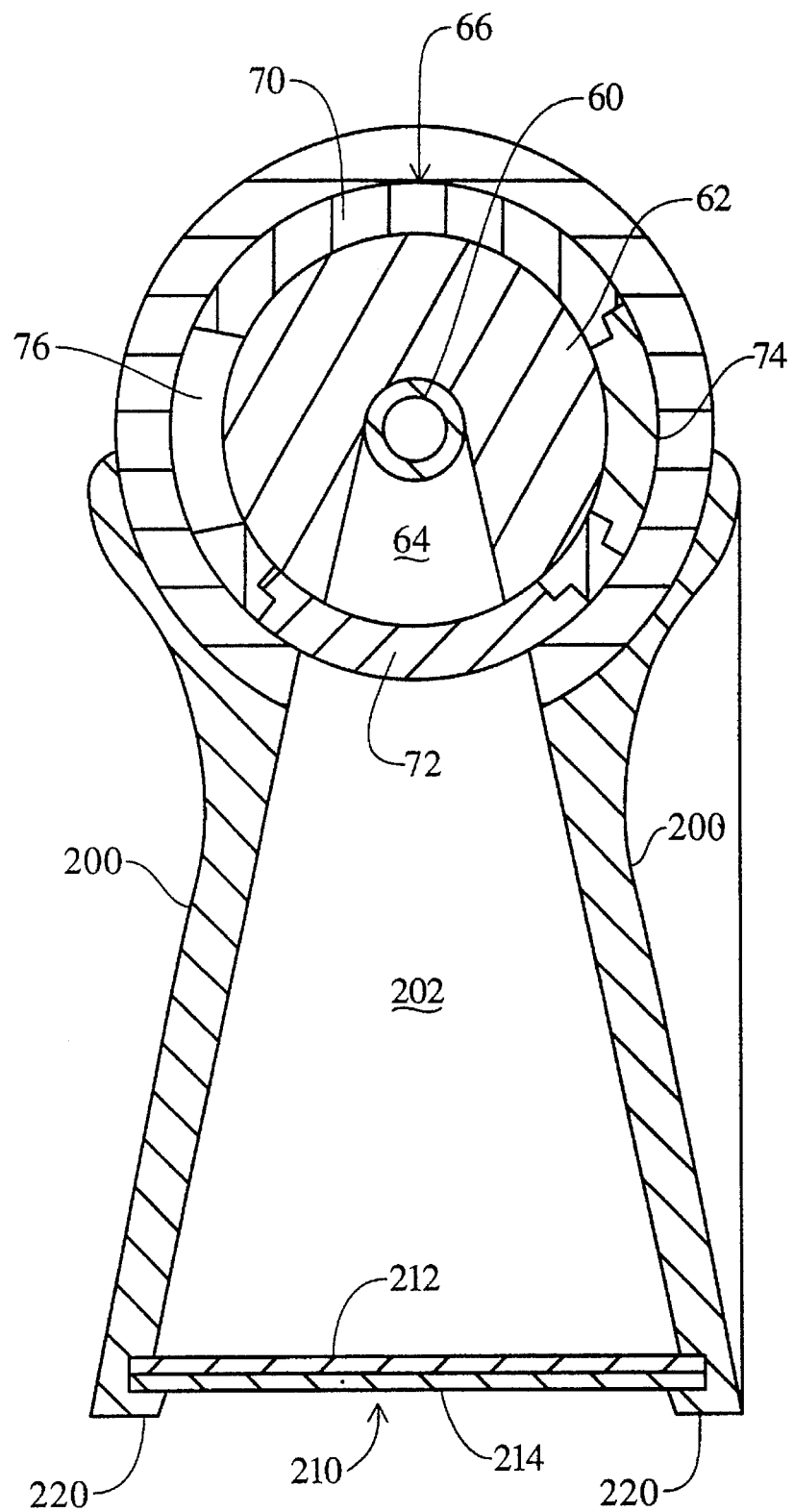
FIG. 4 is a cross-sectional view through the line source, shutter, and collimator of the line source assembly of FIGS. 1–3.

With continuing reference to FIG. 2 and further reference to FIGS. 4 and 5, the transmission radiation source holder 40 supports a transmission radiation source 60, e.g. a stainless steel tube about the size of a pencil which is filled with a radioisotope. The radiation source is mounted in a lead shield 62 that has an opening 64 for directing radiation toward the examination region. A shutter assembly 66 is mounted for rotation around the radiation source. The shutter includes an aluminum cylinder or frame 70. The aluminum cylinder supports a radiation blocking or lead circular arc segment 72 which is positioned in front of the opening 64 when the shutter is closed. The aluminum cylinder also supports a tin arc segment 74 which is aligned with the opening 64 when the collimator is rotated 90° clockwise (in FIG. 4) to a calibration position. The shutter cylinder further includes an opening 76 which is aligned with opening 64 when the cylindrical shutter is rotated counter-clockwise to the open position. The shutter is rotatable between the closed, calibrate, and open position by the electromechanical drive mounted to rotatable gantry portion 16. A manual knob 78 located on the face of the transmission radiation source holder 40 provides a visual indication of the position of the shutter 66.

With particular reference to FIGS. 5, and 6, in order to prevent the operator or a technician from inadvertently opening the shutter when the assembly is not attached to a scanner, a mechanical interlock system 80 is provided. More specifically, the interlock system 80 mounts the transmission radiation source and collimator assembly 40, 42 to the radial positioning means 44 on the rotating gantry portion.

A clamping ring 84 receives a pair of mounting studs 86 from the gantry portion and rotates about 50° to twist and cam lock the assembly 40, 42 to the mounting studs. A pin 88 extends from the clamping ring through an arced aperture 90 to engage a limit switch 92 in the fully locked-on position. The switch 92, thus, provides an electrical feedback to the control panel 32 indicating that the assembly 40, 42 has been locked into place. One or more guide pins 94 assure that the assembly 40, 42 is mounted in the proper orientation.

Once the assembly 40, 42 is locked to the gantry assembly, a shutter coupling clutch assembly 100 connects the shutter 66 with an electromechanical drive 102. The electromechanical drive engages a shutter drive coupling 104 which is connected with an internal drive coupling 106 by a spring biased ball assembly 108. The internal transfer coupling 106 includes a pin 110 that engages a slot 112 in the shutter 66. An end drive sleeve 114 has an arcuate aperture through which the pin 110 extends. The drive end sleeve 114 further has a pin 116 for engaging a slot 118 in the lead line source holder shield 62 to fix the angular orientation of opening 64. A gantry mounted lever 120 selectively lifts the ball 108 against the spring bias decoupling the internal drive member 106 from the shutter drive member 104. This releases the shutter such that it can be manually rotated by the knob 78.

A lockup assembly 130 locks the shutter in the closed position with lead segment 72 across opening 64 unless the assembly 40, 42 is locked to the gantry. The lockup assembly includes a pin 132 which is slidably received in a steel sleeve 134 in the holder assembly. When the shutter 66 is in the closed position, an aperture in a steel guideway 136 in the shutter 66 is aligned with the pin 132. The head of the pin is received in a camway 138 in a shutter locking cam ring 140 which is affixed to the clamping ring 84. (It should be noted that in the exploded view of FIG. 5, the clamping ring 84 is illustrated positioned on the right side of locking pin 132. When the assembly is completed, the clamping ring 84 is in actuality on the left side of locking pin 132. The locking pin 132 is, in this manner, received between the clamping ring 84 and the shutter locking ring cam 140.) The cam 138 raises radially outward as the clamping ring 84 approaches its closed position to lift the locking pin from the shutter 66, releasing the shutter for rotation.

It will further be noted that in order to rotate the clamping ring 84 to remove the assembly, the cam surface 138 must be permitted to cam the locking pin into the aperture in the shutter. If the shutter is not closed and the aperture is not aligned with the locking pin, then the cam 138 will be unable to cam the locking pin downward and will lock the clamping ring 84 against rotation. Hence, the mechanical interlock 80 cannot be released to remove the line source/collimator assembly 40, 42 from the gantry unless the shutter is in the closed position.

The lockup assembly 130 further includes a pin 142 mounted to the radial drive mechanism 44 fixed to the gantry. The pin extends through an aperture in member 144 to engage a locking element 146. The pin 142 lifts the locking element 146 against the bias of a spring 148 out of a seat in member 144 permitting the clamping ring 84 and locking member 146 to be rotated. To remove the assembly from the gantry, the clamping must be rotated to the position in which (1) the pin 132 is received in guideway 136 and (2) locking element 146 is biased against pin 142. Upon removal, the locking element 146 is seated in member 144 locking the clamping ring against rotation preventing the pin 132 from being lifted.

The shutter 66 has an extending pin 150 which engages through an inner race of a needle bearing 152 which rotatably supports the outer end of the shutter end 66 to the knob 78. The bearing portion of shutter 66 is notched to connect with a ball and spring detent assembly 154 to a housing portion 156 to provide positioning in the calibrate position. A limit switch 158 is engaged by a groove in the shutter when the shutter is in the calibration position to provide a positive electrical indication thereof.

In order to replace the line source 60, a plug 160 is removed from the line source holder 62. The plug 160 has a keyed end 162 which is adapted to receive a uniquely configured key member. In this manner, access to the radioactive line source is denied to other than a designated key operator.

The radiation line source 60 is preferably filled with a radioisotope that has a half-life, between 6 hrs and 300 days. Because this half-life is much shorter than the life of a SPECT camera, the line source must be accessible to be replaced from time to time.

With reference again to FIGS. 3 and 4, the collimator means 42 includes a pair of lead side walls 200 which diverge at an angle which enables transmission radiation to span the examination region 12. A plurality of thin septa 202 are mounted between the side walls 200. The septa 202 are constructed of a material which has good radiation stopping power and which, when struck by radiation, emits a gamma ray of relatively low energy, e.g. below 50 keV. Preferably, the septa are constructed of tin or an alloy of tin and antimony. Tin emits gamma rays with a characteristic energy of about 30 keV. Other suitable materials for the septa include metals with an atomic number of about 30–70, particularly tin, antimony, zirconium, niobium, molybdenum, germanium, yttrium, cerium, gadolinium, terbium, dysprosium, holmium, erbium, ruthenium, rhodium, palladium, silver, cadmium, indium, tellurium, cesium, barium, and alloys thereof. Of these, tin, antimony, molybdenum, zirconium, and cadmium are preferred for their more ready availability. The side walls of the collimator 200 could also be made of such materials. However, because many scans call for placing the detector heads as closely adjacent as possible, the transmission radiation source and collimator preferably have as narrow a profile as possible. To this end, the greater stopping power of lead, or other high atomic number material, which permits the side walls 200 to be thinner is preferred. It will be noted that the surface area of the septa which are exposed to radiation from the line source is many times greater than the surface area of the side walls. Optionally, the side walls may be covered or plated on their exposed inside surfaces with tin or one of the other above-discussed metals to limit the emission of the 88 keV characteristic x-rays of lead.

A filter 210 extends across an outlet aperture of the collimator 42. The filter includes an inner layer 212 of a material which stops substantially all of the 88 keV energy x-rays from the lead in the side walls of the collimator, yet passes a substantial portion of the radiation from the transmission line source 60. The filter 210 further includes an outer layer 214 which stops substantially all of the lower energy radiation emitted by the inner layer 212 and by the septa 202. In the preferred embodiment in which the septa are tin or tin/antimony alloy, the inner layer 212 is also tin or tin/antimony and the outer layer 214 is aluminum. The aluminum not only absorbs gamma rays in the 30 keV range, but provide structural strength to the softer tin. Of course, the same alternate metals which can be used to construct the septa can also be used for the inner filter.

Further to the preferred embodiment, the housing has overhanging portions 220 which define a filter receiving track therebetween. A family of filters are provided. The family of filters have varying thicknesses of the inner layer 212. For example, the inner layer 212 in one of the filters may be of an appropriate thickness to absorb about half of the transmission radiation from the radiation source 60. Another of the filters might have a thinner tin portion such that only about ¼ of the radiation is absorbed. Another one might only absorb ¹/₁₀ of the radiation, and so on. As the radiation source decays, the filters are replaced with filters which attenuate a progressively smaller percent of the radiation. In this manner, the output from the transmission line source assembly can be kept substantially constant over two or more half-lives of the radioisotope in the transmission radiation source. A projection 222 and matching detent 224 in the filters act to snap the filters into position against the natural resiliency of the filter metal. For simplicity of construction and for an assured secure fit, it is preferred that all filters of the family have the same thickness, at least adjacent the edges. Thus, as the tin or more radiation attenuative layer becomes thinner, the aluminum layer becomes thicker.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A nuclear camera system comprising:

a stationary gantry portion;

a rotary gantry portion rotatably mounted to the stationary gantry portion for circumferential movement around an examination region;

at least one nuclear camera detector head mounted to the rotary gantry portion for rotation therewith, the nuclear camera detector head having a radiation sensitive face facing toward the examination region;

a transmission radiation source assembly mounted to the rotary gantry portion across the examination region from the nuclear radiation detector head, the transmission radiation source assembly including:

a transmission radiation source, a shutter for selectively allowing and preventing radiation from the transmission radiation source to be transmitted from the radiation source across the examination region to the nuclear camera detector head, a collimator for collimating radiation emerging from the transmission radiation source, and a locking means for selectively locking the transmission radiation source assembly to the rotating gantry portion and releasing the transmission radiation source assembly from the rotating gantry portion, such that the transmission radiation source assembly is selectively removable.

2. The camera system as set forth in claim 1 further including a safety interlock means for locking the shutter in a closed position, the safety interlock means being released by interconnection of the transmission radiation source assembly with the rotating gantry portion.

3. The camera system as set forth in claim 2 wherein the rotating gantry portion includes a key member which is selectively received in the transmission radiation source assembly for releasing the interlock means.

4. The camera system as set forth in claim 1 wherein the transmission radiation source is a line source including an elongated, tube of a radioactive material, the tube of radioactive material being sheathed with a radiation absorbing sheath, the radiation absorptive sheath having a radiation passing slot facing toward the examination region and wherein the shutter includes a cylinder rotatably mounted around the radiation absorbing sheath.

5. A nuclear camera system comprising:

a stationary gantry portion;

a rotary gantry portion rotatably mounted to the stationary gantry portion for circumferential movement around an examination region;

at least one nuclear camera detector head mounted to the rotary gantry portion for rotation therewith, the nuclear camera detector head having a radiation sensitive face facing toward the examination region;

a transmission radiation source assembly mounted to the rotary gantry portion across the examination region from the nuclear radiation detector head, the transmission radiation source assembly including:

a transmission radiation source, a shutter having a shutter cylinder rotatably mounted surrounding the transmission radiation source for selectively allowing and preventing radiation from the transmission radiation source to be transmitted from the radiation source across the examination region to the nuclear camera detector head, the shutter cylinder including a lead segment for blocking the emission of transmission radiation in a closed position, an open segment for passing radiation freely in an open position, and a partially radiation transmissive portion for passing filtered radiation in a calibration position, and a collimator for collimating radiation emerging from the transmission radiation source.

6. The camera system as set forth in claim 5 further including an electromechanical means for moving the shutter cylinder between the open, closed, and calibration positions.

7. The camera system as set forth in claim 5 further including a manual knob means for rotating the shutter.

8. The camera system as set forth in claim 7 further including a safety interlock which locks the shutter in the closed position against rotation, mounting the transmission radiation source assembly to the rotating gantry portion releasing the safety interlock unlocking the shutter.

9. A nuclear camera system comprising:

a stationary gantry portion;

a rotary gantry portion rotatably mounted to the stationary gantry portion for circumferential movement around an examination region;

at least one nuclear camera detector head mounted to the rotary gantry portion for rotation therewith, the nuclear camera detector head having a radiation sensitive face facing toward the examination region;

a transmission radiation source assembly mounted to the rotary gantry portion across the examination region from the nuclear radiation detector head, the transmission radiation source assembly including:

a transmission radiation source, a shutter for selectively allowing and preventing radiation from the transmission radiation source to be transmitted from the radiation source across the examination region to the nuclear camera detector head, and a collimator for collimating radiation emerging from the transmission radiation source, the collimator including a pair of side walls and a plurality of septa extending therebetween, the septa being disposed parallel to a selected radiation path, such that radiation travelling along the selected radiation path pass therebetween and radiation which deviates from the selected path is blocked by the septa, the septa being constructed of a radiation absorbing material from the group consisting of tin, antimony, zirconium, niobium, molybdenum, germanium, yttrium, cerium, gadolinium, terbium, dysprosium, holmium, erbium, ruthenium, rhodium, palladium, silver, cadmium, indium, tellurium, cesium, barium, and alloys thereof.

10. The camera system as set forth in claim 9 wherein the septa are constructed of a material in the group consisting of tin and alloys of tin and antimony.

11. The camera system as set forth in claim 9 wherein the collimator side walls are constructed of lead.

12. The camera system as set forth in claim 11 wherein the lead side walls are coated on an inner surface thereof with a material from the group consisting of tin, antimony, zirconium, niobium, molybdenum, germanium, yttrium, cerium, gadolinium, terbium, dysprosium, holmium, erbium, ruthenium, rhodium, palladium, silver, cadmium, indium, tellurium, cesium, barium, and alloys thereof.

13. The camera system as set forth in claim 9 further including a filter connected across a downstream side of the collimator away from the transmission radiation source, the filter including:

an inner layer which passes a substantial portion of radiation from the transmission radiation source and which emits radiation of a lower energy than the transmission radiation source; and an outer layer constructed of a material which blocks the passage of radiation of the lower energy emitted by the inner layer.

14. A nuclear camera system comprising:

a stationary gantry portion;

a rotary gantry portion rotatably mounted to the stationary gantry portion for circumferential movement around an examination region;

at least one nuclear camera detector head mounted to the rotary gantry portion for rotation therewith, the nuclear camera detector head having a radiation sensitive face facing toward the examination region;

a transmission radiation source assembly mounted to the rotary gantry portion across the examination region from the nuclear radiation detector head, the transmission radiation source assembly including:

a transmission radiation source, a shutter for selectively allowing and preventing radiation from the transmission radiation source to be transmitted from the radiation source across the examination region to the nuclear camera detector head, a collimator for collimating radiation emerging from the transmission radiation source, and a filter connected across a downstream side of the collimator away from the transmission radiation source, the filter including:

an inner layer which passes a substantial portion of radiation from the transmission radiation source and which emits radiation of a lower energy than the transmission radiation source; and an outer layer constructed of a material which blocks the passage of radiation of the lower energy emitted by the inner layer.

15. The camera system as set forth in claim 14 wherein the inner layer is of the group consisting essentially of tin, antimony, zirconium, niobium, molybdenum, germanium, yttrium, cerium, gadolinium, terbium, dysprosium, holmium, erbium, ruthenium, rhodium, palladium, silver, cadmium, indium, tellurium, cesium, barium, and alloys thereof, and wherein the outer layer is from the group consisting essentially of aluminum, copper, alloys of aluminum, and alloys of copper.

16. The camera system as set forth in claim 14 wherein the filter is readily replaceable and further including a plurality of replacement filters, the plurality of replacement filters including filters with inner layers of different thickness such that filters with a thinner inner layer can be selectively inserted as the radiation source decays.

17. The camera system as set forth in claim 14 further including an image processing means for processing output signals from the detector head responsive to radiation from radiopharmaceuticals injected into a subject in the examination region into an image representation and for correcting the radiopharmaceutical image representation in accordance with electrical signals from the detector head responsive to transmission radiation from the transmission radiation source.

18. The camera system as set forth in claim 17 further including a video monitor for converting selected portions of the image representation into a human readable display.

19. The radiation source and collimator assembly for a SPECT camera system, the radiation source and collimator assembly including:

a transmission radiation source;

a shutter for selectively allowing and preventing radiation from the transmission radiation source to be transmitted from the transmission radiation source;

a collimator for collimating radiation emerging from the transmission radiation source;

a connecting means for selectively connecting and releasing the radiation source and collimator assembly to an associated SPECT camera system;

a safety interlock means for locking the shutter in a closed position, the safety interlock means being released by interconnection of the radiation source and collimator assembly with the associated SPECT camera system.

20. The radiation source and collimator assembly as set forth in claim 19 wherein the safety interlock means includes a means which is released by a key on the associated SPECT camera system to permit unlocking of the shutter.

21. A radiation source and collimator assembly for a SPECT camera system, the radiation source and collimator assembly including:

a transmission radiation source including an elongated, tube containing radioactive material and a sheath of radiation absorbing material around the tube, the radiation absorptive sheath having a radiation passing slot a shutter including a cylinder rotatably mounted around the radiation absorbing sheath for selectively allowing and preventing radiation from the transmission radiation source to be transmitted from the transmission radiation source;

a collimator for collimating radiation emerging from the transmission radiation source;

a connector for selectively connecting and releasing the radiation source and collimator assembly to an associated SPECT camera system.

22. The radiation source and collimator assembly as set forth in claim 21 wherein the shutter cylinder includes a lead arc segment for blocking the emission of radiation in a closed position, an open arc segment for passing radiation freely in an open position, and a partially radiation transmissive portion for passing filtered radiation in a calibration position.

23. The radiation source and collimator assembly as set forth in claim 22 further including a safety interlock which selectively locks the shutter cylinder against rotation and in the closed position, the safety interlock being released by a key member to allow the shutter cylinder to rotate when the transmission source and collimator assembly is mounted to an associated structure.

24. A radiation source and collimator assembly for a SPECT camera system, the radiation source and collimator assembly including:

a transmission radiation source;

a shutter for selectively allowing and preventing radiation from the transmission radiation source to be transmitted from the transmission radiation source; and a collimator for collimating radiation emerging from the transmission radiation source to direct the radiation along a selected trajectory, the collimator including a pair of side walls and a plurality of septa extending therebetween, the septa extending parallel to the selected trajectory such that radiation travelling along the selected trajectory passes therebetween and radiation travelling at other than the selected trajectory is absorbed by the septa causing the septa to give off radiation, the septa being constructed from a metal with an atomic number between 30 and 70 such that the radiation given off by the septa is lower in energy than the radiation from the transmission radiation source; and a connector which connects the radiation source and collimator assembly to an associated SPECT camera system.

25. The radiation source and collimator assembly as set forth in claim 24 wherein the septa metal is in the group consisting of tin and alloys of tin and antimony.

26. The radiation source and collimator assembly as set forth in claim 24 wherein the collimator side walls are constructed of lead.

27. The radiation source and collimator assembly as set forth in claim 24 further including a filter connected across a downstream side of the collimator away from the transmission radiation source, the filter including:

an inner layer which passes a substantial portion of radiation from the transmission radiation source and which emits radiation of a lower energy than the transmission radiation source; and an outer layer constructed of a material which blocks the passage of radiation of the lower energy emitted by the inner layer.

28. A radiation source and collimator assembly for a SPECT camera system, the radiation source and collimator assembly including:

a transmission radiation source;

a shutter for selectively allowing and preventing radiation from the transmission radiation source to be transmitted from the transmission radiation source; and a collimator for collimating radiation emerging from the transmission radiation source;

a filter connected across and covering a downstream side of the collimator away from the transmission radiation source to protect the collimator and to filter radiation from the radiation source, the filter including:

an inner layer which passes a substantial portion of radiation from the transmission radiation source and which emits radiation of a lower energy than the transmission radiation source; and an outer layer constructed of a material which blocks the passage of radiation of the lower energy emitted by the inner layer;

a connector for connecting the radiation source and collimator assembly to the associated SPECT camera system.

29. The radiation source and collimator assembly as set forth in claim 28 wherein the inner layer includes a metal with an atomic number between 30 and 70.

30. The radiation source and collimator assembly as set forth in claim 29 wherein the outer layer includes a metal with an atomic number less than 30.

31. The radiation source and collimator assembly as set forth in claim 28 wherein the filter is readily replaceable and further including a plurality of filters, the plurality of filters including filters with inner layers of different thickness such that filters with a thinner inner layer can be selectively inserted as the radiation source decays.

32. The radiation source and collimator assembly as set forth in claim 28 wherein the collimator includes a plurality of septa constructed of a common material as the inner layer.

33. A method of diagnostic imaging comprising:

injecting a subject with a radiopharmaceutical;

receiving radiation from the radiopharmaceutical with a radiation detector head;

transmitting radiation from a radiation source through a radiation filter and through the subject to the detector head, the transmission radiation source including a radioisotope whose radioactivity decays reconstructing an image representation from the radiopharmaceutical radiation and correcting the image representation in accordance with the transmission radiation;

replacing the filter with a series of filters which attenuate the transmitted radiation less as the transmission radiation source decays, such that radiation passing through the filter is held at a substantially constant level as the transmission radiation source radioisotope decays.

34. A method of diagnostic imaging comprising:

injecting a subject with a radiopharmaceutical;

receiving radiation from the radiopharmaceutical with a radiation detector head;

transmitting radiation from a transmission radiation source that gives off higher energy gamma rays through a collimator which includes septa and side walls;

absorbing some of the higher energy gamma rays with the septa and side walls, the septa and side walls giving off lower energy gamma rays in response to the absorbed higher energy gamma rays;

attenuating the lower energy gamma rays with a filter;

transmitting transmission radiation that has passed through the filter through the subject to the detector head;

reconstructing an image representation from the radiopharmaceutical radiation and correcting the image representation in accordance with the transmission radiation.

35. A method of diagnostic imaging comprising:

injecting a subject with a radiopharmaceutical;

receiving radiation from the radiopharmaceutical with a radiation detector head;

transmitting radiation from a transmission radiation source through a collimator which includes septa and side walls, at least a portion of the septa and side walls being constructed of lead which emits 88 keV radiation in response to being irradiated;

with a first layer of the filter, converting the 88 keV radiation from the collimator to a lower energy radiation;

with a second layer of the filter, attenuating the lower energy radiation;

transmitting radiation from the filter through the subject to the detector head;

reconstructing an image representation from the radiopharmaceutical radiation and correcting the image representation in accordance with the radiation from the transmission radiation source.

36. A method of diagnostic imaging comprising:

injecting a subject with a radiopharmaceutical;

receiving radiation from the radiopharmaceutical with a radiation detector head that is mounted on a SPECT camera gantry;

transmitting radiation from a transmission radiation source which is detachably mounted to the SPECT camera gantry across the subject form the detector head;

locking a shutter which opens and closes the transmission radiation source in a closed position whenever the radiation source assembly is detached from the camera gantry;

opening the shutter and passing radiation from the transmission radiation source through a radiation filter and through the subject to the detector head;

reconstructing an image representation from the radioisotope radiation and correcting the image representation in accordance with the transmission radiation.

37. In a SPECT camera assembly which includes a transmission radiation source which emits radiation of a characteristic energy contained in a radiation source holder, a shutter for selectively allowing and preventing radiation from the transmission radiation source to be transmitted toward a subject, and a collimator for collimating the radiation transmitted by the transmission radiation source, at least one of the radiation source, shutter, and collimator tending to emit secondary photopeak radiation in response to incident radiation from the transmission radiation source, the improvement comprising:

a means for limiting the secondary photopeak radiation.

38. In the SPECT camera assembly as set forth in claim 37, at least surfaces of the collimator are comprised of a material which has a secondary emission photopeak with an energy level that is significantly lower than the characteristic energy of the transmission radiation source.

39. In the SPECT camera assembly as set forth in claim 38, the secondary photopeak limiting means includes a filter disposed between the collimator and the subject for preferentially absorbing the secondary photopeak radiation.

40. In the SPECT camera assembly as set forth in claim 39, the improvement further including the filter including a material that absorbs the secondary photopeak radiation and reduces an intensity of the transmitted radiation and further including a plurality of such filters of different thickness such that as the transmission radiation source diminishes in strength, progressively thinner filters are substituted.

41. In the SPECT camera assembly as set forth in claim 38, the improvement further including the secondary photopeak absorbing material being selected from the group consisting of: tin, antimony, zirconium, niobium, molybdenum, germanium, yttrium, cerium, gadolinium, terbium, dysprosium, holmium, erbium, ruthenium, rhodium, palladium, silver, cadmium, indium, tellurium, cesium, barium, and alloys thereof, but not lead.

42. In the SPECT camera assembly as set forth in claim 41 further characterized by the collimator including a plurality of thin septa of the secondary photopeak absorbing material.

43. In the SPECT camera assembly as set forth in claim 37, the improvement further including a connecting means for selectively connecting the radiation source, shutter, and collimator to the SPECT camera system and a safety interlock which locks the shutter in a closed position when the radiation source and collimator assembly are removed from the SPECT camera system.

44. In the SPECT camera assembly as set forth in claim 43, the improvement further including the safety interlock locking the radiation source, shutter, and collimator against removal from the SPECT camera system when the shutter is not closed.

45. In a method of diagnostic imaging in which a subject is injected with a radiopharmaceutical having a first characteristic energy and in which radiation from a transmission radiation source having a second characteristic energy is transmitted from the transmission radiation source, through a collimator, through the subject, and to a detector head, part of the radiation from the radiation source striking internal surfaces of the transmission radiation source and collimator causing the emission of secondary photopeak radiation, the improvement comprising:

limiting the secondary photopeak radiation passing through the patient.

46. The method as set forth in claim 45, the secondary photopeak radiation limiting step including absorbing the secondary photopeak radiation.

47. In the method of diagnostic imaging as set forth in claim 46, the improvement further comprising:

attenuating the transmission radiation with a filter that preferentially absorbs the secondary photopeak radiation when the transmission radiation source is new and as the transmission radiation source ages, replacing the filter with a thinner filter such that the transmission radiation output remains substantially constant over time.

\* \* \* \* \*